(12) United States Patent
Retti et al.

(10) Patent No.: US 12,102,848 B2
(45) Date of Patent: Oct. 1, 2024

(54) ELECTRICALLY ACTIVE RESPIRATOR MASK

(71) Applicant: GridKicker, LLC, Baltimore, MD (US)

(72) Inventors: Kahrl Retti, Parkville, MD (US); Nicholas Richard Retti, Parkville, MD (US)

(73) Assignee: GridKicker, LLC, Baltimore, MD (US)

(*) Notice: Subject to any disclaimer, the term of this patent is extended or adjusted under 35 U.S.C. 154(b) by 554 days.

(21) Appl. No.: 17/244,572

(22) Filed: Apr. 29, 2021

(65) Prior Publication Data

US 2021/0339060 A1 Nov. 4, 2021

Related U.S. Application Data

(60) Provisional application No. 63/018,382, filed on Apr. 30, 2020.

(51) Int. Cl.
| | |
|---|---|
| *A62B 18/02* | (2006.01) |
| *A61L 9/014* | (2006.01) |
| *A61L 9/16* | (2006.01) |
| *A62B 18/08* | (2006.01) |
| *A62B 23/02* | (2006.01) |
| *B33Y 80/00* | (2015.01) |
| *H02J 7/00* | (2006.01) |
| *B33Y 10/00* | (2015.01) |

(52) U.S. Cl.
CPC ............ *A62B 18/025* (2013.01); *A61L 9/014* (2013.01); *A61L 9/16* (2013.01); *A62B 18/08* (2013.01); *A62B 18/084* (2013.01); *A62B 23/02* (2013.01); *B33Y 80/00* (2014.12); *H02J 7/0013* (2013.01); *A61L 2209/14* (2013.01); *B33Y 10/00* (2014.12); *H02J 7/0047* (2013.01)

(58) Field of Classification Search
CPC . A41D 13/1161; A62B 18/025; A62B 18/084; A62B 18/08; A62B 18/04; A62B 18/045; A62B 18/02; A62B 23/00–06; A62B 18/00; A61L 9/014; A61L 9/16; A61L 2209/14; B33Y 80/00; B33Y 10/00; H02J 7/0013; H02J 7/0047
See application file for complete search history.

(56) References Cited

FOREIGN PATENT DOCUMENTS

KR 20160004280 U * 10/2016

* cited by examiner

*Primary Examiner* — Ophelia A Hawthorne
(74) *Attorney, Agent, or Firm* — Dickinson Wright PLLC

(57) ABSTRACT

Provided is an electrically active breathing mask. The mask contains conductive layers separated by insulating layers, the conductive layers being alternatingly positively or negatively charged. Air passing through one insulating layer is directed across the surface of a next charged layer, before flowing through a next insulating layer, and so on. Particles including virus in water vapor or sputum are evaporated as they contact alternately charged layers.

14 Claims, 6 Drawing Sheets

ELECTRICALLY ACTIVE RESPIRATOR MASK

INCORPORATION BY REFERENCE

The application claims the benefit under 35 U.S.C. 119(f) of U.S. Provisional Application No. 63/018,382 filed Apr. 30, 2021, the entire contents of which are hereby incorporated by reference.

BACKGROUND OF THE INVENTION: DESCRIPTION OF THE CURRENT ART

Current state of the art in the field of respirator masks is deficient in the prevention of the spread of viral and bacteriological germs. The current art teaches everything from using spun filtration media such as Hepa filters, cloth facial surrounds combining silver threads as well as copper in washable masks, to masks having additives in the form of germicidal agents such as salts. All of these masks have deficiencies. In the case of the spun as well as the cloth media, the act of washing the media leads to its rapid decay. In the case of additives, the masks become deactivated over the course of time, as well as having limits to length of time the mask may be worn safely. Both types of masks having media cannot effectively block the inhalation of microbes smaller than 3 microns. Current virus strains can have diameters as small as 0.125 microns in diameter, allowing microbes to "slip by" the filtration media.

In addition to these drawbacks, the strapping and sealing of the masks to the wearers face can cause discomfort to the wearer. Further, air passage is restricted is some cases so severely that the wearer can pass out due to hypoxia.

OBJECT OF THE INVENTION

It is the object of the current invention to overcome these deficiencies by using instantaneous electrical evaporation of the microbes upon inhalation and exhalation. A second line of defense against the incoming microbes comes by means of the release of copper and silver ions. It is well known in the art that these types of viruses carry a positive net biasing. By using a series of charged plates, with atmosphere as the dielectric, negatively biased copper ions are released, which bind to positively biased microbes. This is well known in the art to kill RNA based viruses. A third line of defense comes from the positively biased outer most conductive plates (composed of silver, a known antimicrobial) which repel airborne microbes by virtue of its bias.

Deficiencies regarding the resistance to airflow are overcome in the current invention by use of staggered slats that direct the airflow at right angles over the conductive plates. By using slats that are separated by membranes, aeration aperture size is greatly reduced while allowing near normal air flow through the masks.

Strapping is improved by using a strap design that does not contact the wearer's face, while providing sufficient elastic pressure to maintain a seal around the mouth and nose of the wearer. Also, because the air flow is far less compromised, a vacuum effect is not introduced in the mask, which causes burst capillaries in the skin. One only has to observe health care workers who wear current respirators for long periods to see strap damage to the face and burst capillaries around the facial surround. The facial surround of the current embodiment comprises two gasketing contact points, resulting in twice the seal at half the elastic pressure.

SUMMARY OF THE INVENTION

The present application is directed to an electrically active breathing mask. The mask contains conductive layers separated by insulating layers, the conductive layers being alternatingly positively or negatively charged. Air passing through one insulating layer is directed across the surface of a next charged layer, before flowing through a next insulating layer, and so on.

According to one aspect of embodiments of this disclosure, an insulating standoff layer is formed as one layer of parallel slats having a gap therebetween, with a hexagon patterned layer formed on top of the slats to bind the slats together while maintaining their separation.

BRIEF DESCRIPTION OF THE DRAWING FIGURES

FIG. 4 and FIG. 4a illustrate interaction of the mask described in this application with small particles encountered in air;

Throughout the drawing figures like reference numbers should be understood to refer to like elements, features or structure.

DESCRIPTION OF THE INVENTION

An exemplary embodiment of the respiration device described herein is (shown in FIG. 1.) is designed to filter out particulate matter from the airstream including viruses, bacteria, mold spores, pollen, and other irritants. The invention comprises a soft rubber surround (shown in FIG. 1 at 1). Shown at (2) is a hard plastic housing (detachable) containing the electric plates described in the previous text. Shown at (3) is the rubber strap extension that prevents the strap from contacting the wearers face. The strap extension is preferably rigid near the mask, and flexible away from the mask to facilitate wrapping around the user's head while keeping the elastic straps from irritating the user's face. This can be accomplished by 3D printing with a transition from a rigid material to a flexible material, or by any other suitable means of constructing the strap extension from different materials. Shown at (4) is the power supply module that is connected to the charging plates and is under discrete microprocessor control. This module is also detachable for charging purposes or when the mask is being cleaned. Shown at (5) is the outer most rubber membrane that prevents the user from touching the first charged plate. At (6) is shown the rubber attachment point for the elastic strap.

Figure 1:
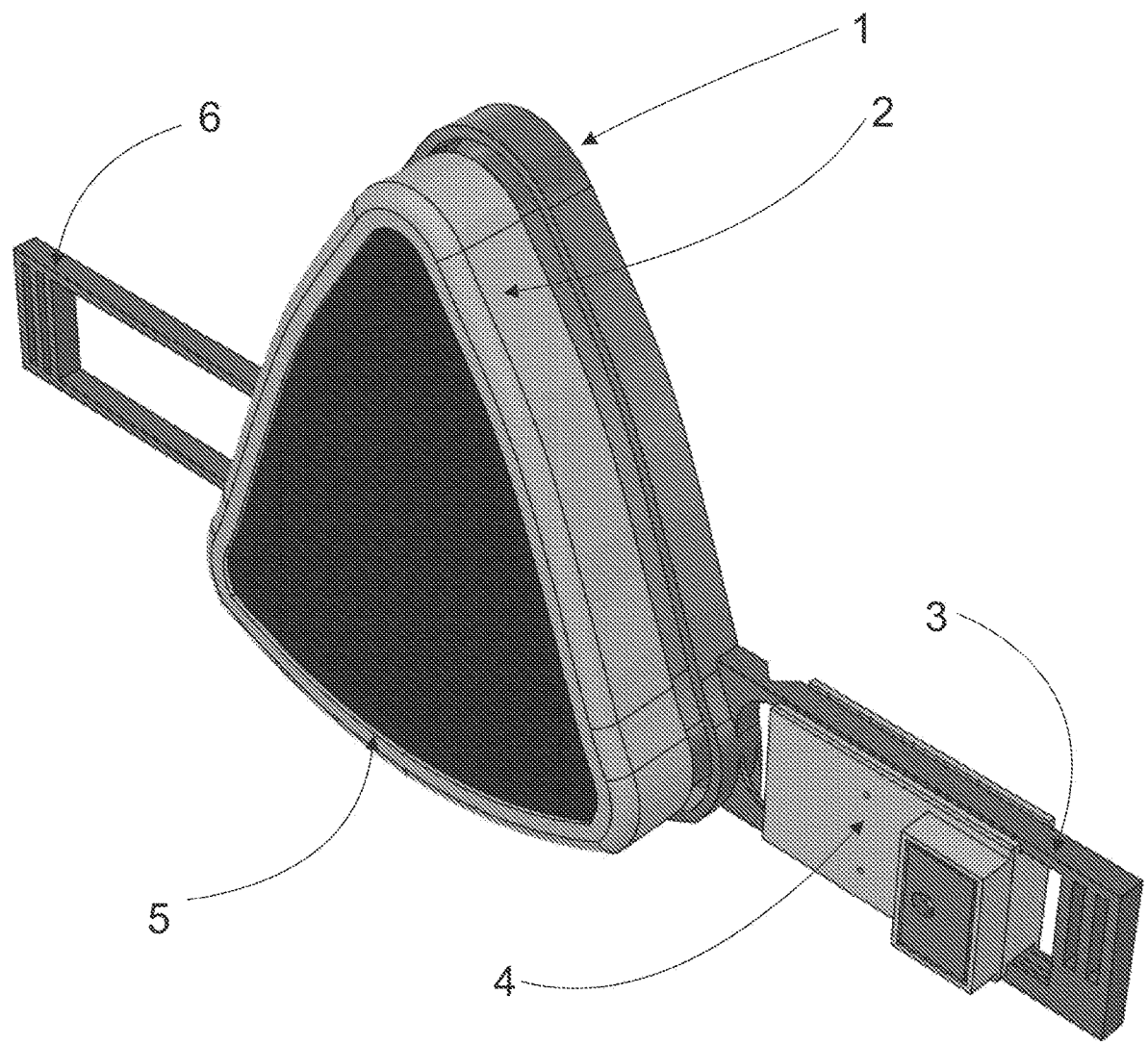
FIG. 1 is an isometric view of an electrically charged breathing mask according to an exemplary embodiment of the invention.
Figure 2:
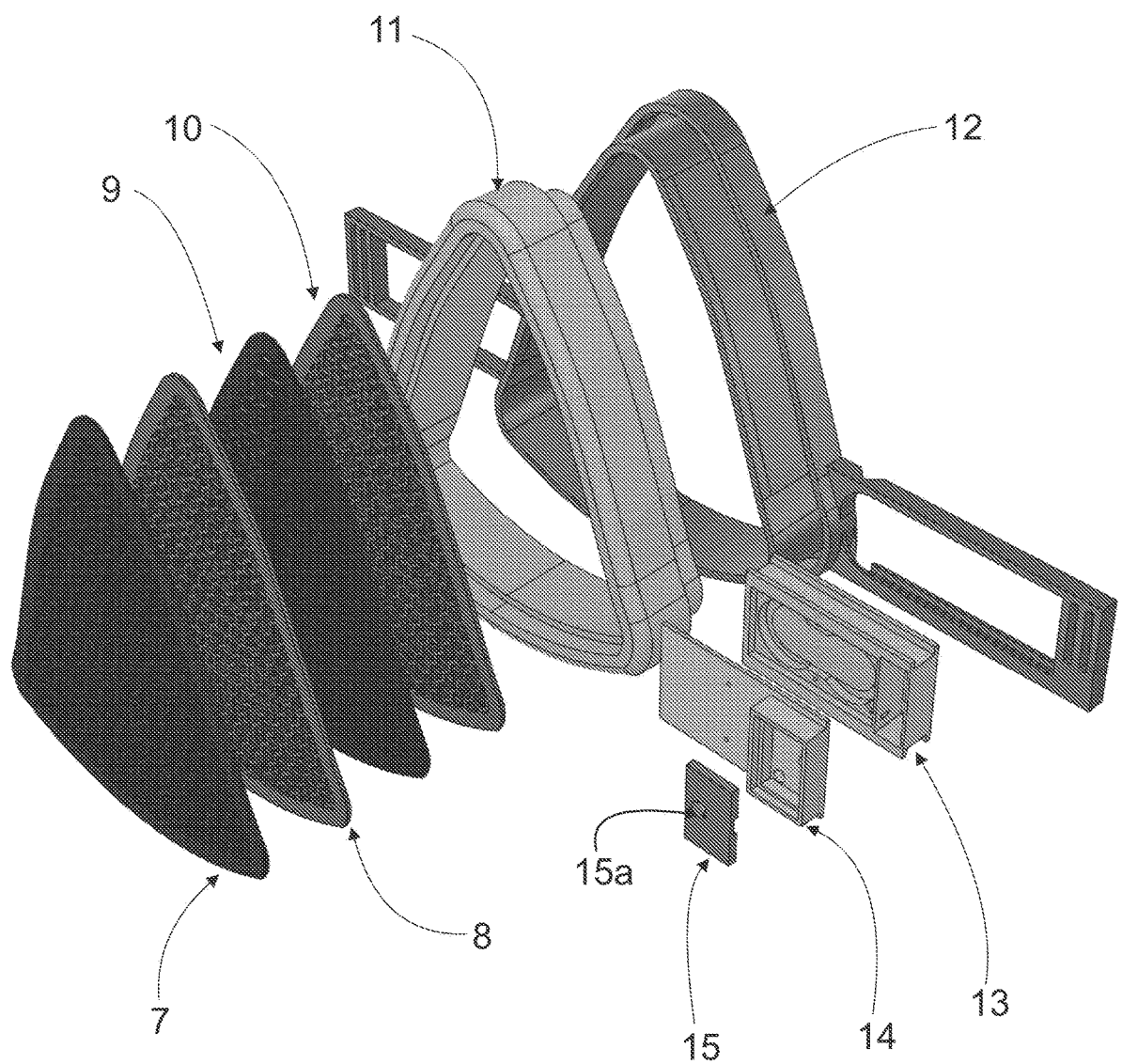
FIG. 2 is an exploded view of the electrically charged breathing mask of FIG. 1.

FIG. 2 is an exploded view of the exemplary embodiment showing at (7) the first rubber layer, (also shown at (5) in FIG. 1). On the back of this first layer, a silver bearing positively biased fabric used in the RF shielding industry having a thread count of 300 strands per inch is attached, allowing airflow through to the second membrane (shown at 8). On the back of the second membrane is attached a fine copper mesh, having spatial distancing between the conductive wires of 200 microns, carrying a negative charge. At (9) is shown a third rubber membrane which has on its back another silver layer (as previously described) which has a positive charge. At (10) is shown a final rubber layer, installed so as to prevent the wearer from contacting the charge plates. At (11) is shown the outer conductive plate housing that surrounds the charged plates, and also provides means of electrical connection to the power module. Shown at (12) are the rubber gasket and strap attachments. At (13) is shown the back of the power control module (PCM) showing the battery cavity. At (14) is the PCM lid, showing the microprocessor cavity, and at (15) its lid with LED indicator Light (15a).

Figure 3:
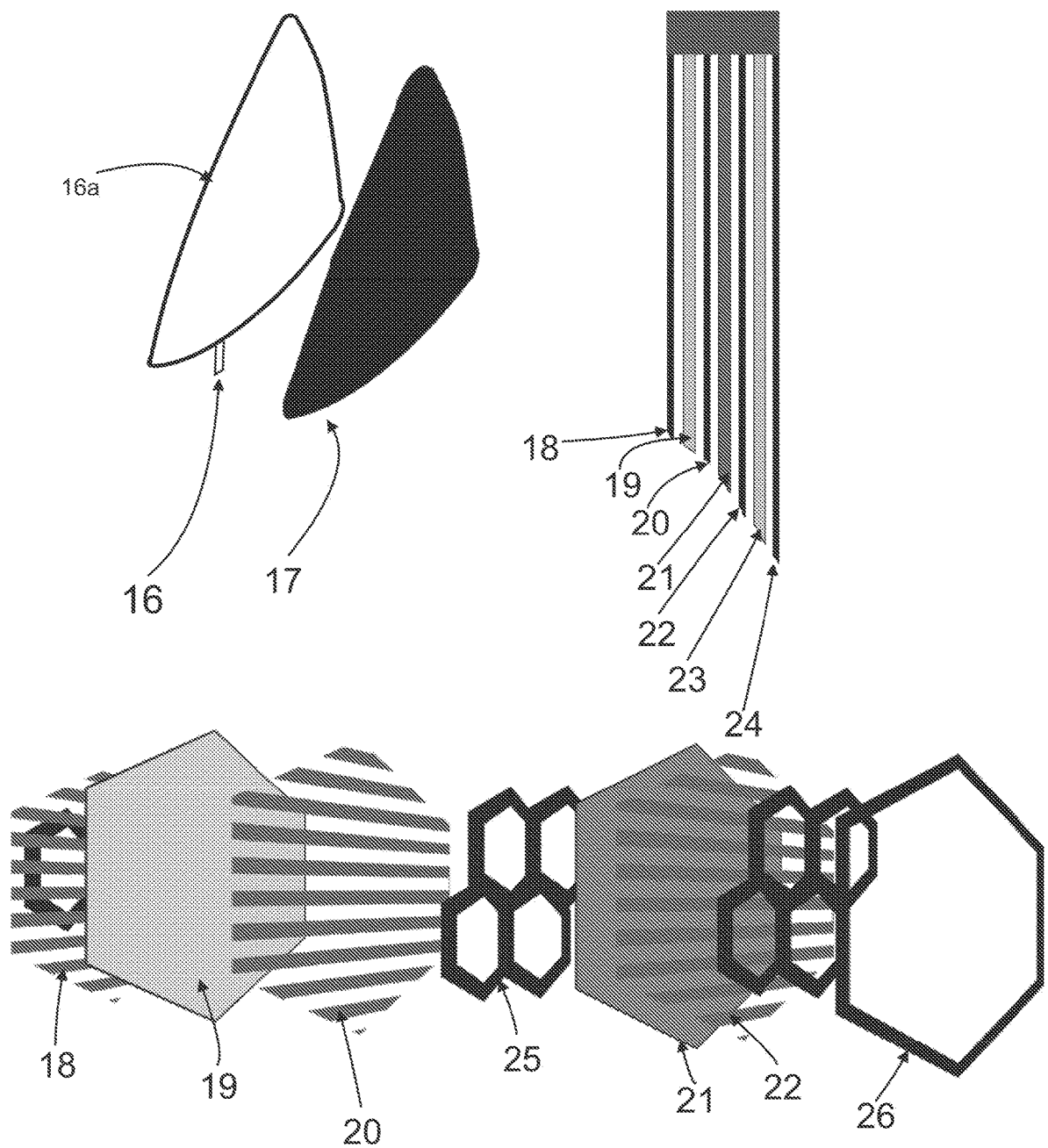
FIG. 3 is a detailed view of the layers of the electrically charged breathing mask of FIGS. 1 and 2.

FIG. 3 shows details regarding the charging plates that comprise the electrical evaporation unit. At (16a) is shown (in outline form) the first conductive plate of silver attached to the back of the first rubber membrane (shown in FIG. 1 at (5)). First conductive layer is so formed as to provide an electrode (16) formed at its edge to connect to a corresponding electrode in the hard outer shell, shown in FIG. 1 at (2).

The electrode is formed as a male to plug into a corresponding female plug socket in the hard outer shell, allowing the charge plates to be removed for replacement or cleaning. The socket in the hard outer shell is then connected by wire to the PCM. Shown at (17) is the first rubber layer shown in FIG. 2 at (7). Shown at (18-24) is a side cross-sectional view of the charge plates and their rubber separation layers. At (18) is shown the first rubber layer, (19) a layer of silver RF fabric, (20) a second rubber layer, (21) a layer of fine copper mesh, (22) a third rubber layer, (23) a second layer of silver fabric, at (24) a fourth and final rubber layer. Shown at (25) is a view of the composition of the rubber membranes, highlighting the hexagonal standoff separation layer. At (26) is shown the rubber gasket surround that forms a seal between the rubber layer and the hard outer shell.

The Mask in Operation

Figure 4:
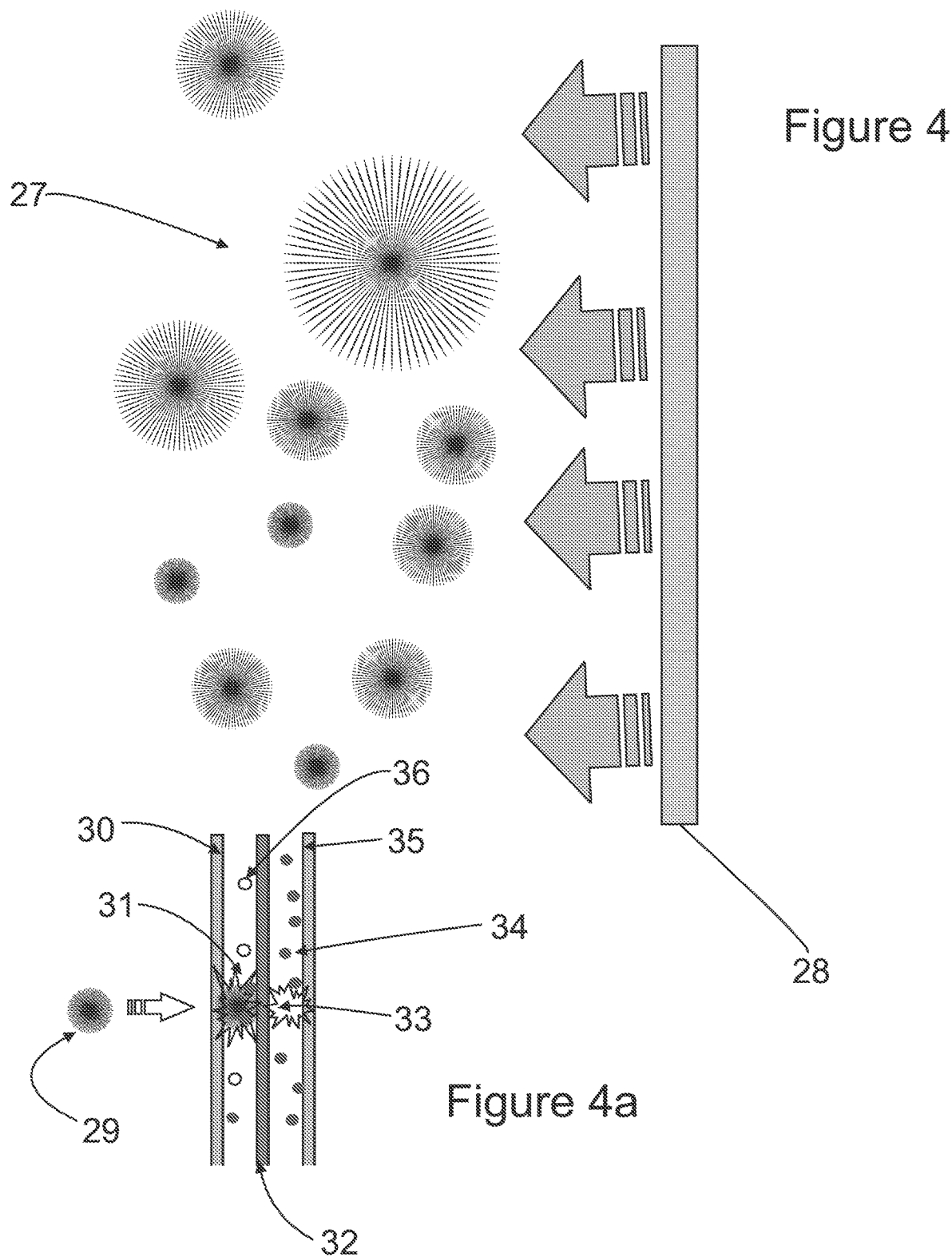

Shown in FIG. 4 is a general operating depiction of the exemplary embodiment. Depicted at (27) are airborne microbes and other pollutants. The majority of these particles are carried by water vapor or human sputum, in the range of 0.5 microns to 3 microns. As the wearer breathes in, these particles are drawn toward the mask, encountering the first silver layer (28). Having a positive net charge on the plate results in the repulsion of the vast majority of these particles, which also carry a net positive bias. Shown in FIG. 4a, at (29) are particles that pass through the first silver layer (30) encountering the negative copper layer (32) and becoming vaporized as a result of a short circuit created by the sputum or water vapor in the air connecting the gap between the two oppositely charged plates (shown at (31). Particles passing through the copper layer (32) encounter a second silver layer (35) and become vaporized at that point (33). As a result of the water vapor or sputum encountering the copper layer, negatively biased copper ions (34) are released which bind themselves to microbes by magnetic attraction. It is well known in the art that copper and silver ions kill a wide variety of microbes. Unbound copper ions are cleaned from the air stream as they encounter the positively biased second silver layer shown at (35). Similarly, the positively biased silver ions will collect on the negatively charged copper plate, preventing inhalation by the wearer. The mask operates identically as the wearer exhales, trapping, evaporating and repelling any particulate matter breathed out by the wearer. It should be appreciated by those of ordinary skill in the art that while the exemplary embodiment describes four rubber layers with two silver and one copper layer, additional layers could be added to provide additional filtering capability.

Power Control Modules

Means are provided to operate the mask using batteries to charge the plates under microprocessor control. Control features include a removable battery containment chamber, which may use rechargeable common button cells for powering the charge plates, a disconnect switch which is located in the mask where the mask contacts the wearer at the chin, and turns the unit off when removed, two LED lights, (blue and red) to indicate when the mask is on, (blue) and (red) when the mask requires cleaning. Likewise, the blue LED will not shine when the batteries need to be recharged or replaced.

Figure 5:
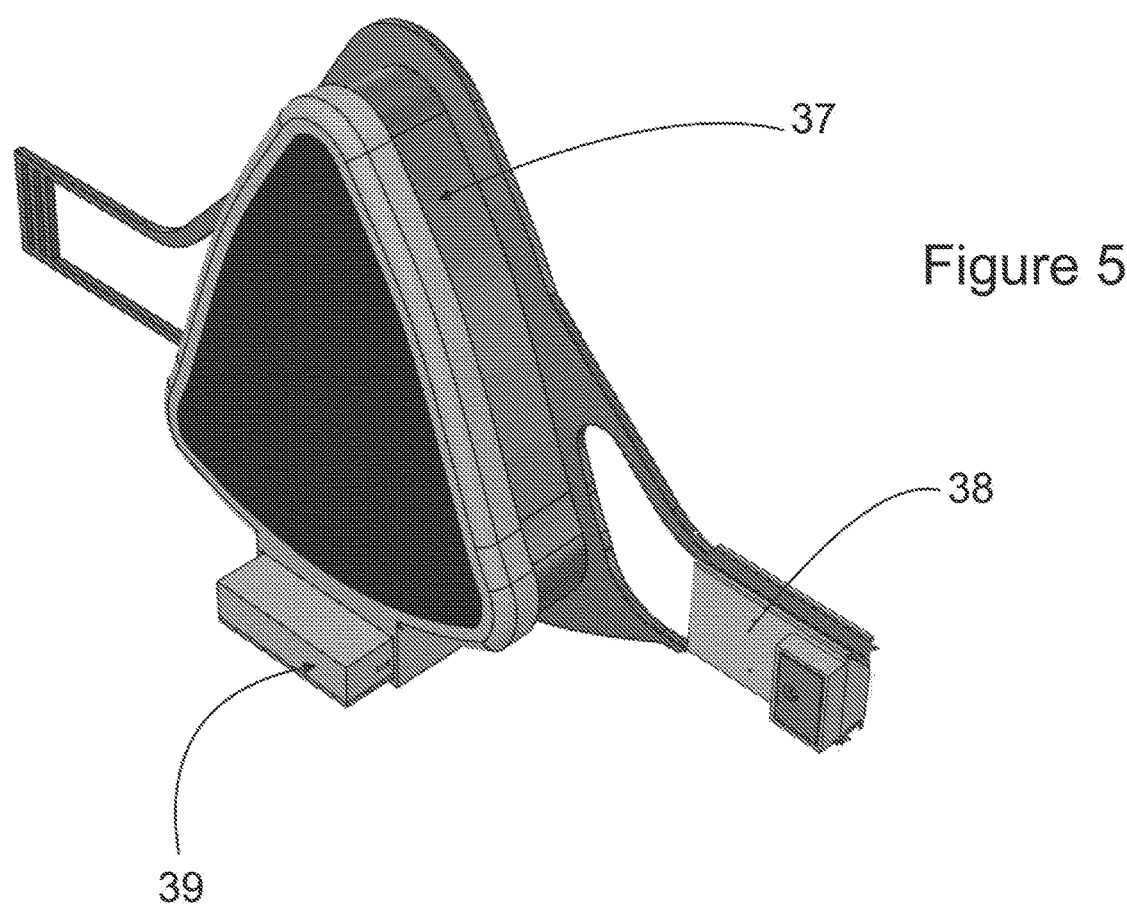
FIGS. 5 and 5a illustrate an alternate embodiment of the electrically charged breathing mask described herein.

Shown in FIG. 5 is another exemplary embodiment showing additional detail regarding the PCMs and their locations in the mask. At (37) we see the rubber facial surround, housing the removable PCM module at (38). An additional module containing batteries as well, is located in the chin area, shown installed at (39).

Figure 5A:
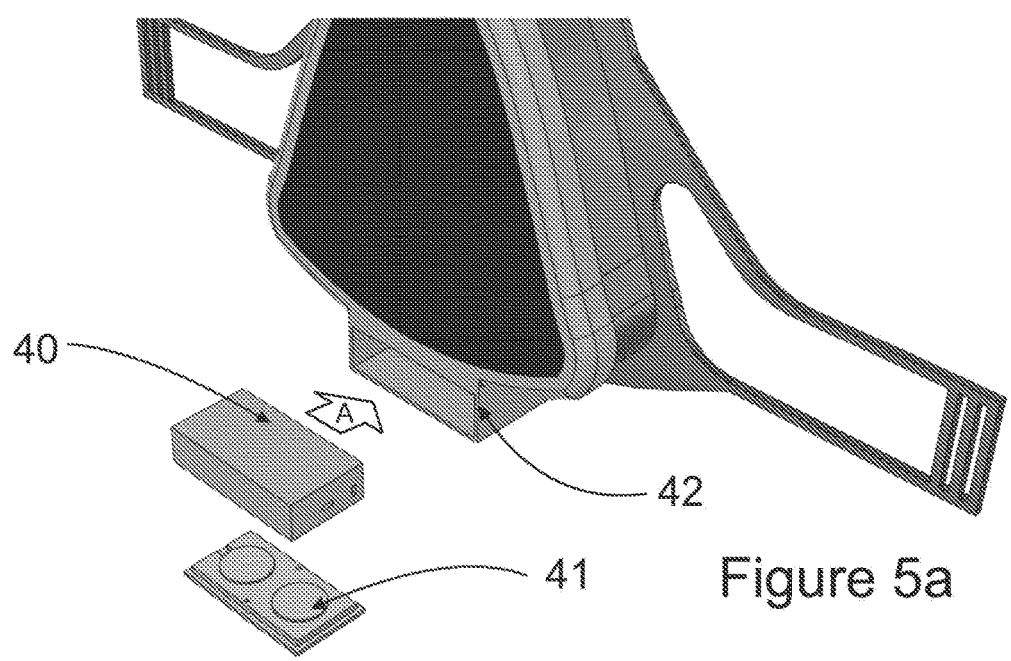

This PCM (39) is removable as well, being slidingly connectable at the indicating arrow (A). Raised contacting electrodes at the back of the PCM at (40) plug into a corresponding receptacle at the base of (42). At (41) is shown the detached back of the PCM showing the location of the two button cell batteries. On the interior of (42), not shown, is the master disconnect lever switch which turns the mask off when not in use. It operates by the means of a lever that contacts the housing at (40) and controls the charge rate of the batteries, the operation of the LEDS, as well as using its internal clock to measure duration of use to determine cleaning cycles. Additionally, the processor can use resistance feedback through the charged plates to determine cleaning cycles. FIG. 5a illustrates yet another exemplary embodiment that includes a PCM in the chin area of the mark only. Of course more PCM's, or PCM's of different sizes may be incorporated into the mask to provide additional power for longer operation without departing from the scope and spirit of the invention.

Improvements in Aeration

Figure 6:
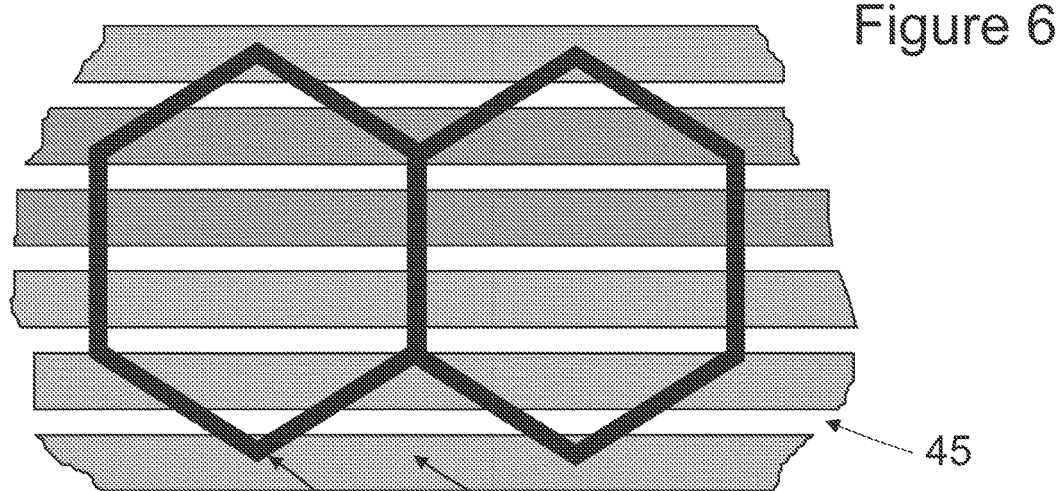
FIGS. 6 and 6a are top and cross sectional views of the insulating standoff layer of a mask according to an exemplary embodiment.

Shown in FIG. 6 is detail of the construction of the rubber separation layers which improve aeration. Shown at (43) is a hexagon stand off pad, which serves to separate the charge plates. The hexagonal structures also bind together the flat separation slats (44) and keep them at a predetermined distance from each other. Close examination of the hexagonal membrane shown in FIG. 3. at (25) shows that the flat slats form a parallel bed of apertures upon which are deposited hexagonal structures that rise above the slats forming an atmosphere trap of sorts that results in a slight compression of air within the hexagon. This rise in air compression results in a greater volume of air that is processed through the charge plates, hence aiding aspiration. The same is true whether the wearer is inhaling or exhaling.

Figure 6A:
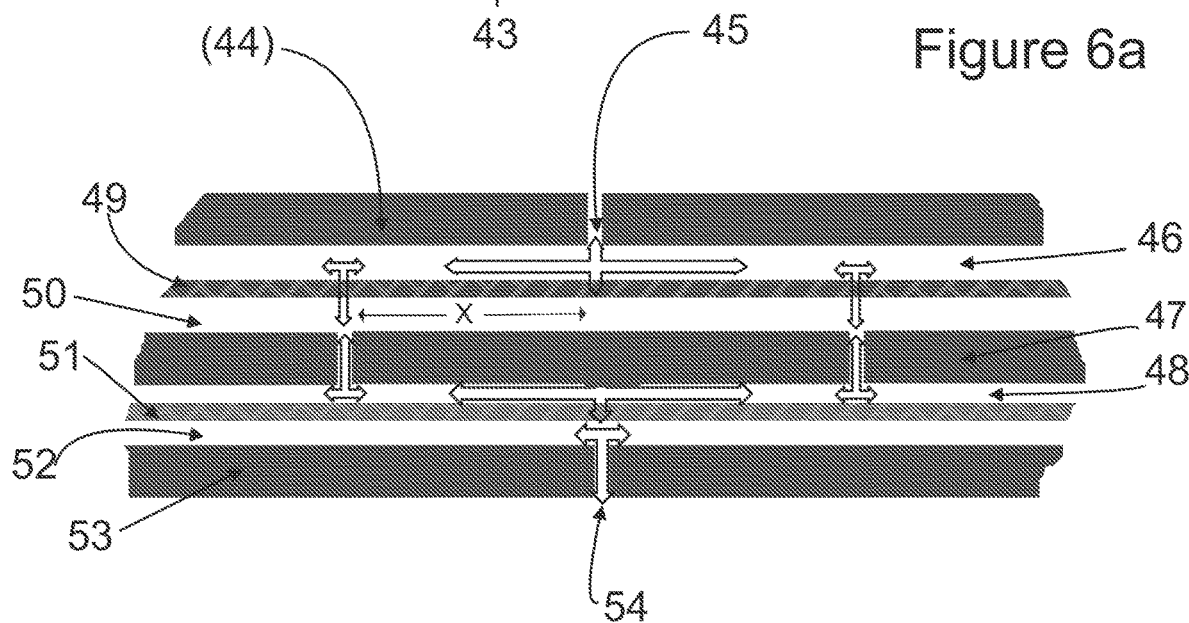

FIG. 6a is a detail drawing of airflow in and around the slats shown at (44) in both figures. Shown at (45) is an edgewise cut away view showing the inlet/outlet opening between the slats. Air passage through this opening shows an air gap (46) between the slats that is created by the stand off hexagons (not shown). These first layer slats are bisected by the succeeding layer of slats (47) in the second separator membrane. This results in a lower pressure area between membranes while a higher air pressure remains in the hexagonal structures. That is, the gaps (45) in respective layers are arranged to be offset as indicated by dimension X. A gap in one layer is preferably located at the lateral midpoint between two caps in a subsequent layer to force air to travel laterally between layers. The bisection of the slats also forces virtually all of the air to travel at right angles to the face of the charge plates, causing a greater exposure to conduction and destruction than if the particles transited through the conductive silver screen and copper screens, shown at (49) and (51) respectively, directly. Further to this, the negatively biased copper plate naturally attracts the positively biased microbes, since there is an increase transiting across the face of the plate, more microbes are captured as well. Shown at (48) is the lower pressure air gap between the second separation layer (47), and the copper charge plate shown at (51). Shown at (52) is another low pressure air gap between the copper plate (51) and the third separation membrane. Shown at (54) is an air gap between slats (44) that allows the air to transit through the succeeding separation membrane and final silver screen (not shown).

Remote Charging and Cleaning

One of the novel features of the invention is its ability to self-clean the charge plates. The hard outer retaining shell is removable from the mask so it may be plugged into an exterior electrical device that is so constructed as to allow a plug to enter shown in FIG. 5a at (42). The plug will allow remote connection to an electrical device that can cycle a higher voltage (than the mask normally uses) through the charge plate eradicating contaminants and through heating of the charge plates. Likewise, the PCM units can be recharged remotely using a charger configured to their operating requirements.

What is claimed:

1. An electrically charged breathing mask, comprising:
   a surround portion oriented to contact a face of a user, and to surround a nose and mouth of the user;
   a housing detachably connected to the surround;
   a rigid strap extension extending laterally from the mask, and having a distal strap attachment point;
   a power supply module;
   a filtration portion formed inside the housing in an airtight manner, and comprising at least one outer electrically insulating layer, and arranged in order from outside to inside, a first conductive layer, and second electrically insulating layer, and second conductive layers, and a third electrically insulating layer;
   wherein the first conductive layer and the second conductive layers are connected to the power supply to charge the first conductive layer with a positive charge and the second conductive layer with a negative charge;
   wherein the outer electrically insulating layer comprises a plurality of parallel slats having a gap therebetween, and bound together by a mesh layer.

2. The electrically charged breathing mask of claim 1, wherein the power module comprises a battery pack attached to the mask.

3. The electrically charged breathing mask of claim 2, further comprising a plurality of battery packs.

4. The electrically charged breathing mask of claim 2, wherein the battery pack comprises a removable battery insertable into a battery receptacle.

5. The electrically charged breathing mask, of claim 1, wherein the second electrically insulating layer is arranged such that gaps between the slats of the outer electrically insulating layer are offset from the gaps between slats of the second electrically insulating layer.

6. The electrically charged breathing mask of claim 5, wherein a space between layers is greater than a width of the gap between slats.

7. The electrically charged breathing mask of claim 1, wherein the mesh layer comprises a hexagonal matrix.

8. The electrically charged breathing mask of claim 1, further comprising an elastic strap removably connected to the distal strap connection of the rigid strap extension such that the elastic strap does not contact a cheek of a user's face.

9. A method of cleaning the mask of claim 1 comprising the step of:
   connecting a high-power power supply to the mask; and
   applying high voltage to the conductive layers of the mask.

10. An insulating standoff layer for an electrically charged breathing mask, comprising:
    A first layer comprising a plurality of slats having a gap therebetween; and
    A mesh layer directly connected to and on top of the first layer, having openings to permit airflow, and binding the slats together and; wherein the plurality of slats are directly connected to the mesh layer.

11. The insulating standoff layer of claim 10, wherein the mesh layer is a hexagonal matrix.

12. The insulating standoff layer of claim 10, wherein the insulating standoff layer is formed from rubber.

13. A method of forming an insulating standoff layer for an electrically charged breathing mask, comprising the steps of:
    forming a first layer of plurality slats formed in a first plane, such that there is a gap between the plurality of slats;
    forming a second layer comprising a mesh of openings that permit airflow directly on top of the first layer and such that the plurality of slats are bound directly to the mesh.

14. The method of claim 13, wherein the forming steps comprising printing the layers with a 3D printer.

* * * * *